(12) United States Patent
Lee

(10) Patent No.: US 11,583,430 B2
(45) Date of Patent: Feb. 21, 2023

(54) SKIN CONTACT MATERIAL

(71) Applicant: CONVATEC LTD., Deeside (GB)

(72) Inventor: Stewart Lee, Skillman, NJ (US)

(73) Assignee: CONVATEC LTD., Bridgewater, NJ (US)

( * ) Notice: Subject to any disclaimer, the term of this patent is extended or adjusted under 35 U.S.C. 154(b) by 648 days.

(21) Appl. No.: 16/121,875

(22) Filed: Sep. 5, 2018

(65) Prior Publication Data

US 2018/0369010 A1    Dec. 27, 2018

Related U.S. Application Data

(63) Continuation of application No. 14/347,996, filed as application No. PCT/GB2012/052132 on Aug. 31, 2012, now Pat. No. 10,092,441.

(30) Foreign Application Priority Data

Sep. 2, 2011 (GB) ..................................... 1115182

(51) Int. Cl.
*A61F 13/00* (2006.01)
*A61F 5/445* (2006.01)
(Continued)

(52) U.S. Cl.
CPC .......... *A61F 5/443* (2013.01); *A61F 13/0253* (2013.01); *A61L 15/28* (2013.01);
(Continued)

(58) Field of Classification Search
CPC .. A61F 2013/00246; A61F 2013/00676; A61F 2013/00702; A61F 2013/00748; A61F 2013/00757; A61F 2013/0077; A61F 2013/00855; C09J 183/04; C09J 7/22; C09J 7/38; C09J 105/00; C09J 105/02; C09J 105/04; C09J 105/06; C09J 105/08; C09J 105/10; C09J 105/12; C09J 105/14; C09J 105/16; C09J 101/00; C09J 101/102;
(Continued)

(56) References Cited

U.S. PATENT DOCUMENTS 2,399,545 A * 4/1946 Davis ................... A61F 13/0226
                                                   604/389
2,940,868 A * 6/1960 Albert ................. A61F 13/0203
                                                   427/2.31
(Continued)

FOREIGN PATENT DOCUMENTS

EP    0353972 A1 *  7/1990 ............. A61F 13/02
EP    3187204 A1    7/2017
(Continued)

*Primary Examiner* — Kim M Lewis
(74) *Attorney, Agent, or Firm* — Taft Stettinius & Hollister LLP; Ryan O. White; Derek B. Lavender

(57) ABSTRACT

A substrate based skin contact material formed from a hydrocolloid having a silicone based component extending over regions of the substrate surface. The adhesive is formed non-continuously over the substrate to provide areas devoid of adhesive to allow appreciable moisture transfer between the skin and substrate and improve the skin friendliness of the material during use and allow convenient removal with avoidance of skin irritation.

16 Claims, 3 Drawing Sheets

(51) Int. Cl.
*C09J 7/20* (2018.01)
*A61F 5/443* (2006.01)
*A61L 15/28* (2006.01)
*A61L 15/58* (2006.01)
*A61L 24/00* (2006.01)
*A61L 24/04* (2006.01)
*A61L 24/08* (2006.01)
*A61L 15/60* (2006.01)
*C09J 7/38* (2018.01)
*C09J 7/22* (2018.01)
*A61F 13/02* (2006.01)
*A61M 25/02* (2006.01)
*C09J 183/04* (2006.01)

(52) U.S. Cl.
CPC .............. *A61L 15/58* (2013.01); *A61L 15/60* (2013.01); *A61L 24/0031* (2013.01); *A61L 24/046* (2013.01); *A61L 24/08* (2013.01); *A61M 25/02* (2013.01); *C09J 7/22* (2018.01); *C09J 7/38* (2018.01); *A61F 2013/0077* (2013.01); *A61F 2013/00246* (2013.01); *A61F 2013/00676* (2013.01); *A61F 2013/00702* (2013.01); *A61F 2013/00748* (2013.01); *A61F 2013/00757* (2013.01); *A61F 2013/00855* (2013.01); *A61M 2025/0266* (2013.01); *C09J 183/04* (2013.01); *Y10T 428/24322* (2015.01); *Y10T 428/24802* (2015.01)

(58) Field of Classification Search
CPC .............. C09J 101/104; C09J 101/106; C09J 101/108; C09J 103/00; A61M 25/02; A61M 2025/0266; A61L 15/28; A61L 15/58; A61L 15/60; A61L 24/0031; A61L 24/046; A61L 24/08; Y10T 428/24322; Y10T 428/24802
USPC ........................................................ 602/55
See application file for complete search history.

(56) References Cited

U.S. PATENT DOCUMENTS

| | | | |
|---|---|---|---|
| 5,009,648 A * | 4/1991 | Aronoff | B32B 27/304 604/332 |
| 5,686,169 A * | 11/1997 | Hassall | B32B 37/1292 428/195.1 |
| 6,206,864 B1 * | 3/2001 | Kavanagh | A61F 5/448 604/332 |
| 9,877,874 B2 * | 1/2018 | Nielsen | A61F 13/025 |
| 10,016,537 B2 | 7/2018 | Menon et al. | |
| 10,046,096 B2 | 8/2018 | Askem et al. | |
| 10,076,447 B2 | 9/2018 | Barta et al. | |
| 10,076,587 B2 | 9/2018 | Locke et al. | |
| 10,143,784 B2 | 12/2018 | Walton et al. | |
| 10,426,670 B2 | 10/2019 | von Blucher et al. | |
| 10,426,747 B2 | 10/2019 | Johnson | |
| 10,426,874 B2 | 10/2019 | Chien et al. | |
| 10,426,875 B2 | 10/2019 | Biott et al. | |
| 10,426,938 B2 | 10/2019 | Locke et al. | |
| 10,434,015 B2 | 10/2019 | Taylor et al. | |
| 10,434,142 B2 | 10/2019 | Niazi et al. | |
| 10,434,210 B2 | 10/2019 | Olson et al. | |
| 10,434,284 B2 | 10/2019 | Hanson et al. | |
| 10,449,094 B2 | 10/2019 | Donda et al. | |
| D866,756 S | 11/2019 | Allen et al. | |
| 10,463,760 B2 | 11/2019 | Karthikeyan et al. | |
| 10,463,773 B2 | 11/2019 | Haggstrom et al. | |
| 10,470,933 B2 | 11/2019 | Riesinger | |
| 10,470,936 B2 | 11/2019 | Wohlgemuth et al. | |
| 10,471,122 B2 | 11/2019 | Shi et al. | |
| 10,471,190 B2 | 11/2019 | Locke et al. | |
| 10,478,345 B2 | 11/2019 | Barta et al. | |
| 10,478,346 B2 | 11/2019 | Knutson | |
| 10,478,394 B2 | 11/2019 | Yu | |
| 10,485,707 B2 | 11/2019 | Sexton | |
| 10,485,891 B2 | 11/2019 | Andrews et al. | |
| 10,485,892 B2 | 11/2019 | Hands et al. | |
| 10,485,906 B2 | 11/2019 | Freedman et al. | |
| 10,486,135 B2 | 11/2019 | Yang et al. | |
| 10,492,956 B2 | 12/2019 | Zamierowski | |
| 10,493,178 B2 | 12/2019 | Marchant et al. | |
| 10,493,184 B2 | 12/2019 | Collinson et al. | |
| 10,493,185 B2 | 12/2019 | Stokes et al. | |
| 10,500,099 B2 | 12/2019 | Hung et al. | |
| 10,500,103 B2 | 12/2019 | Croizat et al. | |
| 10,500,104 B2 | 12/2019 | Sookraj | |
| 10,500,173 B2 | 12/2019 | Yang et al. | |
| 10,500,235 B2 | 12/2019 | Wardell | |
| 10,500,300 B2 | 12/2019 | Dybe et al. | |
| 10,500,301 B2 | 12/2019 | Laurensou | |
| 10,500,302 B2 | 12/2019 | Holm et al. | |
| 10,501,487 B2 | 12/2019 | Andrews et al. | |
| 10,506,928 B2 | 12/2019 | Locke et al. | |
| 10,507,141 B2 | 12/2019 | Allen et al. | |
| 10,507,259 B2 | 12/2019 | Cree et al. | |
| 10,512,707 B2 | 12/2019 | Whalen, III et al. | |
| 10,525,170 B2 | 1/2020 | Havenstrite et al. | |
| 10,532,137 B2 | 1/2020 | Pratt et al. | |
| 10,532,194 B2 | 1/2020 | Locke et al. | |
| 10,537,657 B2 | 1/2020 | Phillips et al. | |
| 10,542,936 B2 | 1/2020 | Goldberg et al. | |
| 10,543,133 B2 | 1/2020 | Shaw et al. | |
| 10,543,293 B2 | 1/2020 | Suschek | |
| 10,548,777 B2 | 2/2020 | Locke et al. | |
| 10,549,008 B2 | 2/2020 | Yoo | |
| 10,549,016 B2 | 2/2020 | Bushko et al. | |
| 10,549,017 B2 | 2/2020 | Hsiao et al. | |
| 10,555,838 B2 | 2/2020 | Wu et al. | |
| 10,555,839 B2 | 2/2020 | Hartwell | |
| 10,556,044 B2 | 2/2020 | Robinson et al. | |
| 10,561,533 B2 | 2/2020 | Hoggarth et al. | |
| 10,561,536 B2 | 2/2020 | Holm et al. | |
| 10,568,767 B2 | 2/2020 | Addison et al. | |
| 10,568,768 B2 | 2/2020 | Long et al. | |
| 10,568,770 B2 | 2/2020 | Robinson et al. | |
| 10,568,771 B2 | 2/2020 | MacDonald et al. | |
| 10,568,773 B2 | 2/2020 | Tuck et al. | |
| 10,568,983 B2 | 2/2020 | Gerdes et al. | |
| 10,575,991 B2 | 3/2020 | Dunn | |
| 10,575,992 B2 | 3/2020 | Sarangapani et al. | |
| 10,576,037 B2 | 3/2020 | Harrell | |
| 10,576,189 B2 | 3/2020 | Locke et al. | |
| 10,583,042 B2 | 3/2020 | Sarangapani et al. | |
| 10,583,228 B2 | 3/2020 | Shuler et al. | |
| 10,589,007 B2 | 3/2020 | Coulthard et al. | |
| 10,590,184 B2 | 3/2020 | Kuo | |
| 10,610,414 B2 | 4/2020 | Hartwell et al. | |
| 10,610,415 B2 | 4/2020 | Griffey et al. | |
| 10,610,623 B2 | 4/2020 | Robinson et al. | |
| 10,617,569 B2 | 4/2020 | Bonn | |
| 10,617,608 B2 | 4/2020 | Shin et al. | |
| 10,617,769 B2 | 4/2020 | Huang | |
| 10,617,784 B2 | 4/2020 | Yu et al. | |
| 10,617,786 B2 | 4/2020 | Kluge et al. | |
| 10,618,266 B2 | 4/2020 | Wright et al. | |
| 10,624,984 B2 | 4/2020 | Courage | |
| 10,625,002 B2 | 4/2020 | Locke et al. | |
| 10,632,019 B2 | 4/2020 | Vitaris | |
| 10,632,224 B2 | 4/2020 | Hardy et al. | |
| 10,639,206 B2 | 5/2020 | Hu et al. | |
| 10,639,350 B2 | 5/2020 | Arber et al. | |
| 10,639,404 B2 | 5/2020 | Lichtenstein | |
| 10,646,614 B2 | 5/2020 | Grinstaff et al. | |
| 10,653,562 B2 | 5/2020 | Robinson et al. | |
| 10,653,782 B2 | 5/2020 | Ameer et al. | |
| 10,653,810 B2 | 5/2020 | Datt et al. | |
| 10,653,821 B2 | 5/2020 | Nichols | |
| 10,653,823 B2 | 5/2020 | Bharti et al. | |
| 10,660,799 B2 | 5/2020 | Wu et al. | |
| 10,660,851 B2 | 5/2020 | Millis et al. | |
| 10,660,992 B2 | 5/2020 | Canner et al. | |

(56) References Cited

U.S. PATENT DOCUMENTS

| | | |
|---|---|---|
| 10,660,994 B2 | 5/2020 | Askem et al. |
| 10,667,955 B2 | 6/2020 | Allen et al. |
| 10,667,956 B2 | 6/2020 | Van Holten et al. |
| 10,682,257 B2 | 6/2020 | Lu |
| 10,682,258 B2 | 6/2020 | Manwaring et al. |
| 10,682,259 B2 | 6/2020 | Hunt et al. |
| 10,682,318 B2 | 6/2020 | Twomey et al. |
| 10,682,386 B2 | 6/2020 | Ellis-Behnke et al. |
| 10,682,446 B2 | 6/2020 | Askem et al. |
| 10,687,983 B2 | 6/2020 | Dahlberg et al. |
| 10,687,985 B2 | 6/2020 | Lee et al. |
| 10,688,215 B2 | 6/2020 | Munro et al. |
| 10,688,217 B2 | 6/2020 | Hanson et al. |
| RE48,117 E | 7/2020 | Albert et al. |
| 10,702,419 B2 | 7/2020 | Locke et al. |
| 10,702,420 B2 | 7/2020 | Hammond et al. |
| 10,703,942 B2 | 7/2020 | Tunius |
| 10,709,760 B2 | 7/2020 | Gronberg et al. |
| 10,709,807 B2 | 7/2020 | Kshirsagar |
| 10,709,883 B2 | 7/2020 | Spector |
| 10,716,711 B2 | 7/2020 | Locke et al. |
| 10,716,874 B2 | 7/2020 | Koyama et al. |
| 10,729,589 B2 | 8/2020 | Dorian et al. |
| 10,729,590 B2 | 8/2020 | Simmons et al. |
| 10,729,826 B2 | 8/2020 | Lin |
| 10,736,787 B2 | 8/2020 | Hannigan et al. |
| 10,736,788 B2 | 8/2020 | Locke et al. |
| 10,736,985 B2 | 8/2020 | Odermatt et al. |
| 10,737,003 B2 | 8/2020 | Fujisaki |
| 10,743,900 B2 | 8/2020 | Ingram et al. |
| 10,744,040 B2 | 8/2020 | Kazala, Jr. et al. |
| 10,744,041 B2 | 8/2020 | Hartwell |
| 10,744,225 B2 | 8/2020 | Lindgren et al. |
| 10,744,237 B2 | 8/2020 | Guidi et al. |
| 10,744,238 B2 | 8/2020 | Guidi et al. |
| 10,744,239 B2 | 8/2020 | Armstrong et al. |
| 10,744,240 B2 | 8/2020 | Simmons et al. |
| 10,751,212 B2 | 8/2020 | Raza et al. |
| 10,751,442 B2 | 8/2020 | Bonnefin et al. |
| 10,751,452 B2 | 8/2020 | Topaz |
| 10,758,423 B2 | 9/2020 | Pigg et al. |
| 10,758,424 B2 | 9/2020 | Blott et al. |
| 10,758,425 B2 | 9/2020 | Blott et al. |
| 10,758,426 B2 | 9/2020 | Eddy |
| 10,758,651 B2 | 9/2020 | Blott et al. |
| 10,765,561 B2 | 9/2020 | Lattimore et al. |
| 10,765,783 B2 | 9/2020 | Locke et al. |
| 10,772,767 B2 | 9/2020 | Bjork et al. |
| 10,772,999 B2 | 9/2020 | Svensby |
| 10,779,993 B2 | 9/2020 | Bishop et al. |
| 10,780,114 B2 | 9/2020 | Udagawa et al. |
| 10,780,194 B2 | 9/2020 | Flach et al. |
| 10,780,201 B2 | 9/2020 | Lin |
| 10,780,202 B2 | 9/2020 | Askem et al. |
| 10,780,203 B2 | 9/2020 | Coulthard et al. |
| 10,782,238 B2 | 9/2020 | Hicks et al. |
| 10,792,191 B2 | 10/2020 | Robinson et al. |
| 10,792,192 B2 | 10/2020 | Tout et al. |
| 10,792,337 B2 | 10/2020 | Leung et al. |
| 10,792,404 B2 | 10/2020 | Hu et al. |
| 10,792,482 B2 | 10/2020 | Randolph et al. |
| 10,800,905 B2 | 10/2020 | Delli-Santi et al. |
| 10,806,819 B2 | 10/2020 | Shuler |
| 11,020,277 B2 | 6/2021 | Wilkes et al. |
| 11,033,436 B2 | 6/2021 | Holm et al. |
| 11,058,587 B2 | 7/2021 | Adie et al. |
| 11,076,997 B2 | 8/2021 | Hunt et al. |
| 11,090,195 B2 | 8/2021 | Adie et al. |
| 11,090,196 B2 | 8/2021 | Gowans et al. |
| 11,116,669 B2 | 9/2021 | Gowans et al. |
| 11,141,521 B2 | 10/2021 | Beadle et al. |
| 11,147,716 B2 | 10/2021 | Taylor et al. |
| 11,154,426 B2 | 10/2021 | Riesinger |
| 11,154,649 B2 | 10/2021 | Collinson et al. |
| 11,173,074 B2 | 11/2021 | Love et al. |
| 11,246,757 B2 | 2/2022 | Hartwell et al. |
| 11,246,762 B2 | 2/2022 | Holm et al. |
| 11,247,025 B2 | 2/2022 | Hanson et al. |
| 11,273,077 B2 | 3/2022 | Kubek |
| 11,304,854 B2 | 4/2022 | Wohlgemuth et al. |
| 11,304,855 B2 | 4/2022 | Wohlgemuth et al. |
| 11,318,223 B2 | 5/2022 | Wibaux |
| 11,364,150 B2 | 6/2022 | Gowans et al. |
| 2006/0155260 A1 | 7/2006 | Blott et al. |
| 2006/0172000 A1 | 8/2006 | Cullen et al. |
| 2007/0179461 A1* | 8/2007 | Sambasivam .......... C09J 183/04 604/336 |
| 2007/0185426 A1 | 8/2007 | Ambrosio et al. |
| 2007/0219512 A1 | 9/2007 | Heaton et al. |
| 2007/0239078 A1 | 10/2007 | Jaeb |
| 2009/0069764 A1* | 3/2009 | Burlot .................... A61F 5/448 604/345 |
| 2009/0234307 A1 | 9/2009 | Vitaris |
| 2009/0259203 A1 | 10/2009 | Hu et al. |
| 2009/0293887 A1 | 12/2009 | Wilkes et al. |
| 2009/0299303 A1 | 12/2009 | Seegert |
| 2010/0015208 A1 | 1/2010 | Kershaw et al. |
| 2010/0030178 A1 | 2/2010 | MacMeccan et al. |
| 2010/0125233 A1 | 5/2010 | Edward et al. |
| 2010/0125258 A1 | 5/2010 | Coulthard et al. |
| 2010/0137775 A1 | 6/2010 | Hu et al. |
| 2010/0185163 A1 | 7/2010 | Heagle |
| 2010/0298790 A1 | 11/2010 | Guidi et al. |
| 2011/0015595 A1 | 1/2011 | Robinson et al. |
| 2011/0028918 A1 | 2/2011 | Hartwell |
| 2011/0112457 A1 | 5/2011 | Holm et al. |
| 2011/0178451 A1 | 7/2011 | Robinson et al. |
| 2011/0224593 A1 | 9/2011 | Tunius |
| 2011/0224630 A1 | 9/2011 | Simmons et al. |
| 2011/0230849 A1 | 9/2011 | Coulthard et al. |
| 2011/0251566 A1 | 10/2011 | Zimnitsky et al. |
| 2011/0257572 A1 | 10/2011 | Locke et al. |
| 2011/0257573 A1 | 10/2011 | Hong et al. |
| 2011/0275972 A1 | 11/2011 | Rosenberg |
| 2012/0071845 A1 | 3/2012 | Hu et al. |
| 2012/0130332 A1 | 5/2012 | Cotton et al. |
| 2012/0136325 A1 | 5/2012 | Allen et al. |
| 2012/0209226 A1 | 8/2012 | Simmons et al. |
| 2013/0053795 A1 | 2/2013 | Coulthard |
| 2013/0123728 A1 | 5/2013 | Pratt et al. |
| 2013/0226063 A1 | 8/2013 | Taylor et al. |
| 2014/0005618 A1 | 1/2014 | Locke et al. |
| 2014/0074053 A1 | 3/2014 | Locke et al. |
| 2014/0188060 A1 | 7/2014 | Robinson et al. |
| 2014/0194838 A1 | 7/2014 | Wibaux |
| 2014/0200532 A1 | 7/2014 | Robinson et al. |
| 2014/0236112 A1 | 8/2014 | Von Wolff et al. |
| 2014/0256925 A1 | 9/2014 | Catchmark et al. |
| 2014/0276499 A1 | 9/2014 | Locke et al. |
| 2014/0296804 A1 | 10/2014 | Hicks et al. |
| 2014/0308338 A1 | 10/2014 | Nierle et al. |
| 2014/0309574 A1 | 10/2014 | Cotton |
| 2015/0018433 A1 | 1/2015 | Leipzig et al. |
| 2015/0057624 A1 | 2/2015 | Simmons et al. |
| 2015/0071985 A1 | 3/2015 | Walker et al. |
| 2015/0079152 A1 | 3/2015 | Wuollett et al. |
| 2015/0094674 A1 | 4/2015 | Pratt et al. |
| 2015/0104486 A1 | 4/2015 | Bonnefin et al. |
| 2015/0112311 A1 | 4/2015 | Hammond et al. |
| 2015/0119831 A1 | 4/2015 | Robinson et al. |
| 2015/0119834 A1 | 4/2015 | Locke et al. |
| 2015/0141941 A1 | 5/2015 | Allen et al. |
| 2015/0148785 A1 | 5/2015 | Kleiner |
| 2015/0174304 A1 | 6/2015 | Askem et al. |
| 2015/0245949 A1 | 9/2015 | Locke et al. |
| 2015/0246164 A1 | 9/2015 | Heaton et al. |
| 2015/0250979 A1 | 9/2015 | Loske |
| 2015/0265741 A1 | 9/2015 | Duncan et al. |
| 2015/0265743 A1 | 9/2015 | Hanson et al. |
| 2015/0320901 A1 | 11/2015 | Chandrashekhar-Bhat et al. |
| 2016/0008293 A1 | 1/2016 | Shi et al. |
| 2016/0038626 A1 | 2/2016 | Locke et al. |
| 2016/0051724 A1 | 2/2016 | Sahin et al. |
| 2016/0067107 A1 | 3/2016 | Cotton |

(56) References Cited

U.S. PATENT DOCUMENTS

| | | |
|---|---|---|
| 2016/0100987 A1 | 4/2016 | Hartwell et al. |
| 2016/0106878 A1 | 4/2016 | Yang et al. |
| 2016/0106892 A1 | 4/2016 | Hartwell |
| 2016/0166422 A1 | 6/2016 | Karim et al. |
| 2016/0193244 A1 | 7/2016 | Ota et al. |
| 2016/0222548 A1 | 8/2016 | Agboh |
| 2016/0271178 A1 | 9/2016 | Hauser et al. |
| 2016/0287743 A1 | 10/2016 | Andrews |
| 2016/0339158 A1 | 11/2016 | Collinson et al. |
| 2016/0374847 A1 | 12/2016 | Lachenbruch et al. |
| 2017/0014275 A1 | 1/2017 | Schneider |
| 2017/0049111 A1 | 2/2017 | Patton et al. |
| 2017/0072669 A1 | 3/2017 | Sekido et al. |
| 2017/0128269 A1 | 5/2017 | Coulthard et al. |
| 2017/0189237 A1 | 7/2017 | Locke et al. |
| 2017/0189575 A1 | 7/2017 | Lee et al. |
| 2017/0209615 A1 | 7/2017 | Tornero Garcia et al. |
| 2017/0232161 A1 | 8/2017 | Fewkes et al. |
| 2017/0258956 A1 | 9/2017 | Flach et al. |
| 2017/0367895 A1 | 12/2017 | Holm et al. |
| 2017/0368239 A1 | 12/2017 | Askem et al. |
| 2018/0008742 A1 | 1/2018 | Hoggarth et al. |
| 2018/0014974 A1 | 1/2018 | Hoggarth et al. |
| 2018/0023217 A1 | 1/2018 | Patton et al. |
| 2018/0030321 A1 | 2/2018 | Tunius |
| 2018/0042789 A1 | 2/2018 | Bradford et al. |
| 2018/0078423 A1 | 3/2018 | Magin et al. |
| 2018/0086903 A1 | 3/2018 | Zhang et al. |
| 2018/0118809 A1 | 5/2018 | Mearns Spragg |
| 2018/0133066 A1 | 5/2018 | Ahsani et al. |
| 2018/0140467 A1 | 5/2018 | Hunt |
| 2018/0140822 A1 | 5/2018 | Robinson et al. |
| 2018/0200414 A1 | 7/2018 | Askem et al. |
| 2018/0221531 A1 | 8/2018 | Bender et al. |
| 2018/0236124 A1 | 8/2018 | Young et al. |
| 2018/0243463 A1 | 8/2018 | Chatterjee et al. |
| 2018/0243464 A1 | 8/2018 | Hwang et al. |
| 2018/0244857 A1 | 8/2018 | Lee et al. |
| 2018/0272052 A1 | 9/2018 | Locke et al. |
| 2018/0296397 A1 | 10/2018 | Askem et al. |
| 2018/0303873 A1 | 10/2018 | Been et al. |
| 2018/0311419 A1 | 11/2018 | Locke et al. |
| 2018/0333522 A1 | 11/2018 | Pratt et al. |
| 2018/0344533 A1 | 12/2018 | Rovaniemi |
| 2018/0353334 A1 | 12/2018 | Locke et al. |
| 2018/0353337 A1 | 12/2018 | Locke |
| 2018/0353339 A1 | 12/2018 | Locke et al. |
| 2018/0353340 A1 | 12/2018 | Robinson et al. |
| 2018/0353344 A1 | 12/2018 | Locke et al. |
| 2018/0353662 A1 | 12/2018 | Locke et al. |
| 2018/0353663 A1 | 12/2018 | Locke et al. |
| 2018/0360667 A1 | 12/2018 | Droche |
| 2019/0000677 A1 | 1/2019 | Munro |
| 2019/0015258 A1 | 1/2019 | Gowans et al. |
| 2019/0015468 A1 | 1/2019 | Yadav et al. |
| 2019/0030223 A1 | 1/2019 | Lin |
| 2019/0046682 A1 | 2/2019 | Choi et al. |
| 2019/0060127 A1 | 2/2019 | Locke et al. |
| 2019/0083752 A1 | 3/2019 | Howell et al. |
| 2019/0117465 A1 | 4/2019 | Osborne et al. |
| 2019/0117466 A1 | 4/2019 | Kazala, Jr. et al. |
| 2019/0117861 A1 | 4/2019 | Locke et al. |
| 2019/0125590 A1 | 5/2019 | Rehbein et al. |
| 2019/0133830 A1 | 5/2019 | Bishop et al. |
| 2019/0151155 A1 | 5/2019 | Bonn |
| 2019/0151159 A1 | 5/2019 | Gowans et al. |
| 2019/0151495 A1 | 5/2019 | Helary et al. |
| 2019/0184052 A1 | 6/2019 | Ilan et al. |
| 2019/0231600 A1 | 8/2019 | Locke et al. |
| 2019/0231602 A1 | 8/2019 | Locke et al. |
| 2019/0231943 A1 | 8/2019 | Robinson et al. |
| 2019/0274889 A1 | 9/2019 | Steward et al. |
| 2019/0282728 A1 | 9/2019 | Kellar et al. |
| 2019/0290799 A1 | 9/2019 | Arshi et al. |
| 2019/0298249 A1 | 10/2019 | Bates et al. |
| 2019/0298577 A1 | 10/2019 | Locke et al. |
| 2019/0298578 A1 | 10/2019 | Shulman et al. |
| 2019/0298579 A1 | 10/2019 | Moore et al. |
| 2019/0298580 A1 | 10/2019 | Hall et al. |
| 2019/0298582 A1 | 10/2019 | Addison et al. |
| 2019/0298881 A1 | 10/2019 | Ramjit et al. |
| 2019/0298882 A1 | 10/2019 | Nelson |
| 2019/0298895 A1 | 10/2019 | Selby et al. |
| 2019/0307611 A1 | 10/2019 | Askem et al. |
| 2019/0307612 A1 | 10/2019 | Hartwell et al. |
| 2019/0307934 A1 | 10/2019 | Allen et al. |
| 2019/0307935 A1 | 10/2019 | Simmons et al. |
| 2019/0314187 A1 | 10/2019 | Emslander et al. |
| 2019/0314209 A1 | 10/2019 | Ha et al. |
| 2019/0314544 A1 | 10/2019 | Filho et al. |
| 2019/0321232 A1 | 10/2019 | Jardret et al. |
| 2019/0321509 A1 | 10/2019 | Chakravarthy et al. |
| 2019/0321526 A1 | 10/2019 | Robinson et al. |
| 2019/0322795 A1 | 10/2019 | Kubo et al. |
| 2019/0328580 A1 | 10/2019 | Emslander et al. |
| 2019/0336343 A1 | 11/2019 | Etchells et al. |
| 2019/0336344 A1 | 11/2019 | Locke |
| 2019/0336345 A1 | 11/2019 | Bannwart |
| 2019/0336346 A1 | 11/2019 | Locke et al. |
| 2019/0336640 A1 | 11/2019 | Vismara et al. |
| 2019/0336641 A1 | 11/2019 | Nisbet |
| 2019/0336643 A1 | 11/2019 | Luukko et al. |
| 2019/0336658 A1 | 11/2019 | Heaton et al. |
| 2019/0336739 A1 | 11/2019 | Locke et al. |
| 2019/0343687 A1 | 11/2019 | Locke et al. |
| 2019/0343889 A1 | 11/2019 | Luukko et al. |
| 2019/0343979 A1 | 11/2019 | Kearney et al. |
| 2019/0343993 A1 | 11/2019 | Weston |
| 2019/0343994 A1 | 11/2019 | Greener |
| 2019/0344242 A1 | 11/2019 | Kim et al. |
| 2019/0350763 A1 | 11/2019 | Pratt et al. |
| 2019/0350764 A1 | 11/2019 | Zochowski et al. |
| 2019/0350765 A1 | 11/2019 | Heagle et al. |
| 2019/0350775 A1 | 11/2019 | Biasutti et al. |
| 2019/0350970 A1 | 11/2019 | Saphier et al. |
| 2019/0351092 A1 | 11/2019 | Silver et al. |
| 2019/0351093 A1 | 11/2019 | Stein et al. |
| 2019/0351094 A1 | 11/2019 | Maher et al. |
| 2019/0351095 A1 | 11/2019 | Maher et al. |
| 2019/0351111 A1 | 11/2019 | Locke et al. |
| 2019/0358088 A1 | 11/2019 | Lavocah et al. |
| 2019/0358361 A1 | 11/2019 | McInnes et al. |
| 2019/0358372 A1 | 11/2019 | Askem et al. |
| 2019/0365948 A1 | 12/2019 | Deegan et al. |
| 2019/0365962 A1 | 12/2019 | Lee et al. |
| 2019/0374408 A1 | 12/2019 | Robles et al. |
| 2019/0374673 A1 | 12/2019 | Hoefinghoff et al. |
| 2019/0380878 A1 | 12/2019 | Edwards et al. |
| 2019/0380881 A1 | 12/2019 | Albert et al. |
| 2019/0380882 A1 | 12/2019 | Taylor et al. |
| 2019/0380883 A1 | 12/2019 | Macphee et al. |
| 2019/0381222 A9 | 12/2019 | Locke et al. |
| 2019/0388577 A1 | 12/2019 | Chandrashekhar-Bhat et al. |
| 2019/0388579 A1 | 12/2019 | Macphee et al. |
| 2019/0388589 A1 | 12/2019 | Macphee et al. |
| 2020/0000640 A1 | 1/2020 | Mondal et al. |
| 2020/0000642 A1 | 1/2020 | Waite |
| 2020/0000643 A1 | 1/2020 | Locke |
| 2020/0000955 A1 | 1/2020 | Andrews et al. |
| 2020/0000956 A1 | 1/2020 | Huang et al. |
| 2020/0000960 A1 | 1/2020 | Kellar et al. |
| 2020/0000985 A1 | 1/2020 | Seddon et al. |
| 2020/0008981 A1 | 1/2020 | Wheldrake |
| 2020/0009289 A1 | 1/2020 | Torabinejad et al. |
| 2020/0009400 A1 | 1/2020 | Ribeiro et al. |
| 2020/0017650 A1 | 1/2020 | Young et al. |
| 2020/0022844 A1 | 1/2020 | Blott et al. |
| 2020/0023102 A1 | 1/2020 | Powell |
| 2020/0023103 A1 | 1/2020 | Joshi et al. |
| 2020/0023104 A1 | 1/2020 | Eriksson et al. |
| 2020/0023105 A1 | 1/2020 | Long et al. |
| 2020/0023106 A1 | 1/2020 | Carroll et al. |
| 2020/0030153 A1 | 1/2020 | Johannison et al. |
| 2020/0030480 A1 | 1/2020 | Choi |

(56) References Cited

U.S. PATENT DOCUMENTS

| | | |
|---|---|---|
| 2020/0030499 A1 | 1/2020 | Menon et al. |
| 2020/0038023 A1 | 2/2020 | Dunn |
| 2020/0038249 A1 | 2/2020 | Pratt et al. |
| 2020/0038250 A1 | 2/2020 | Edwards et al. |
| 2020/0038251 A1 | 2/2020 | Locke et al. |
| 2020/0038252 A1 | 2/2020 | Spiro |
| 2020/0038283 A1 | 2/2020 | Hall et al. |
| 2020/0038470 A1 | 2/2020 | Datt et al. |
| 2020/0038544 A1 | 2/2020 | Grover et al. |
| 2020/0038546 A1 | 2/2020 | Dizio et al. |
| 2020/0038639 A1 | 2/2020 | Patel et al. |
| 2020/0046565 A1 | 2/2020 | Barta et al. |
| 2020/0046566 A1 | 2/2020 | Carey et al. |
| 2020/0046567 A1 | 2/2020 | Carroll et al. |
| 2020/0046568 A1 | 2/2020 | Sexton |
| 2020/0046663 A1 | 2/2020 | Murdock et al. |
| 2020/0046876 A1 | 2/2020 | Liu |
| 2020/0046887 A1 | 2/2020 | Runquist et al. |
| 2020/0054491 A1 | 2/2020 | Hentrich et al. |
| 2020/0054781 A1 | 2/2020 | Weiser et al. |
| 2020/0060879 A1 | 2/2020 | Edwards et al. |
| 2020/0061253 A1 | 2/2020 | Long et al. |
| 2020/0061254 A1 | 2/2020 | Joshi et al. |
| 2020/0061379 A1 | 2/2020 | Bogie et al. |
| 2020/0069476 A1 | 3/2020 | Randolph et al. |
| 2020/0069477 A1 | 3/2020 | Holm et al. |
| 2020/0069479 A1 | 3/2020 | Buan et al. |
| 2020/0069835 A1 | 3/2020 | Hissink et al. |
| 2020/0069850 A1 | 3/2020 | Beadle et al. |
| 2020/0069851 A1 | 3/2020 | Blott et al. |
| 2020/0069853 A1 | 3/2020 | Hall et al. |
| 2020/0078223 A1 | 3/2020 | Locke et al. |
| 2020/0078225 A1 | 3/2020 | Grillitsch et al. |
| 2020/0078305 A1 | 3/2020 | Auvinen et al. |
| 2020/0078330 A1 | 3/2020 | Gay |
| 2020/0078482 A1 | 3/2020 | Yoon et al. |
| 2020/0078499 A1 | 3/2020 | Gadde et al. |
| 2020/0085625 A1 | 3/2020 | Bellini et al. |
| 2020/0085626 A1 | 3/2020 | Braga et al. |
| 2020/0085629 A1 | 3/2020 | Locke et al. |
| 2020/0085630 A1 | 3/2020 | Robinson et al. |
| 2020/0085991 A1 | 3/2020 | Coomber |
| 2020/0085992 A1 | 3/2020 | Locke et al. |
| 2020/0086049 A1 | 3/2020 | Park et al. |
| 2020/0093756 A1 | 3/2020 | Sabacinski |
| 2020/0093953 A1 | 3/2020 | Kim et al. |
| 2020/0093954 A1 | 3/2020 | Leise, III |
| 2020/0093970 A1 | 3/2020 | Hunt et al. |
| 2020/0095421 A1 | 3/2020 | Kettel |
| 2020/0100945 A1 | 4/2020 | Albert et al. |
| 2020/0107964 A1 | 4/2020 | Locke et al. |
| 2020/0107965 A1 | 4/2020 | Greener |
| 2020/0107967 A1 | 4/2020 | Holm et al. |
| 2020/0108169 A1 | 4/2020 | Hu et al. |
| 2020/0113741 A1 | 4/2020 | Rehbein et al. |
| 2020/0114039 A1 | 4/2020 | Wang et al. |
| 2020/0114040 A1 | 4/2020 | Waite et al. |
| 2020/0114049 A1 | 4/2020 | Wall |
| 2020/0121510 A1 | 4/2020 | Hartwell et al. |
| 2020/0121521 A1 | 4/2020 | Daniel et al. |
| 2020/0121833 A9 | 4/2020 | Askem et al. |
| 2020/0129338 A1 | 4/2020 | Gardiner et al. |
| 2020/0129341 A1 | 4/2020 | Coulthard et al. |
| 2020/0129654 A1 | 4/2020 | Bouvier et al. |
| 2020/0129655 A1 | 4/2020 | Gardiner et al. |
| 2020/0129675 A1 | 4/2020 | Robinson et al. |
| 2020/0138754 A1 | 5/2020 | Johnson |
| 2020/0139023 A1 | 5/2020 | Haggstrom et al. |
| 2020/0139025 A1 | 5/2020 | Robinson et al. |
| 2020/0141031 A1 | 5/2020 | Kosan |
| 2020/0146894 A1 | 5/2020 | Long |
| 2020/0155355 A1 | 5/2020 | Hill et al. |
| 2020/0155358 A1 | 5/2020 | Wheldrake |
| 2020/0155361 A1 | 5/2020 | Pigg et al. |
| 2020/0155379 A1 | 5/2020 | Shaw et al. |
| 2020/0163802 A1 | 5/2020 | Hunt et al. |
| 2020/0163803 A1 | 5/2020 | Pigg et al. |
| 2020/0164112 A1 | 5/2020 | Kato et al. |
| 2020/0164120 A1 | 5/2020 | Jaecklein et al. |
| 2020/0170841 A1 | 6/2020 | Waite et al. |
| 2020/0170842 A1 | 6/2020 | Locke |
| 2020/0170843 A1 | 6/2020 | Collinson et al. |
| 2020/0171197 A1 | 6/2020 | Hubbell et al. |
| 2020/0179558 A1 | 6/2020 | Munro et al. |
| 2020/0179673 A1 | 6/2020 | Wan |
| 2020/0188180 A1 | 6/2020 | Akbari et al. |
| 2020/0188182 A1 | 6/2020 | Sanders et al. |
| 2020/0188550 A1 | 6/2020 | Dagger et al. |
| 2020/0188564 A1 | 6/2020 | Dunn |
| 2020/0190310 A1 | 6/2020 | Meyer |
| 2020/0197227 A1 | 6/2020 | Locke et al. |
| 2020/0197228 A1 | 6/2020 | Hartwell |
| 2020/0197559 A1 | 6/2020 | Bourdillon et al. |
| 2020/0197580 A1 | 6/2020 | Kilpadi et al. |
| 2020/0206036 A1 | 7/2020 | Robinson et al. |
| 2020/0214637 A1 | 7/2020 | Brownhill et al. |
| 2020/0214897 A1 | 7/2020 | Long et al. |
| 2020/0214898 A1 | 7/2020 | Waite et al. |
| 2020/0215220 A1 | 7/2020 | Schomburg et al. |
| 2020/0215226 A1 | 7/2020 | Kitagawa et al. |
| 2020/0222469 A1 | 7/2020 | Cotton |
| 2020/0229983 A1 | 7/2020 | Robinson et al. |
| 2020/0237564 A1 | 7/2020 | Hammond et al. |
| 2020/0237816 A1 | 7/2020 | Lait |
| 2020/0246195 A1 | 8/2020 | Robinson et al. |
| 2020/0253785 A1 | 8/2020 | Bernet et al. |
| 2020/0253786 A1 | 8/2020 | Harrison et al. |
| 2020/0254139 A1 | 8/2020 | Phillips et al. |
| 2020/0261275 A1 | 8/2020 | Manwaring et al. |
| 2020/0261276 A1 | 8/2020 | Lujan Hernandez et al. |
| 2020/0268560 A1 | 8/2020 | Harrison et al. |
| 2020/0268561 A1 | 8/2020 | Locke et al. |
| 2020/0270484 A1 | 8/2020 | Lipscomb et al. |
| 2020/0276055 A1 | 9/2020 | Randolph et al. |
| 2020/0276058 A1 | 9/2020 | Locke et al. |
| 2020/0277450 A1 | 9/2020 | Silverstein et al. |
| 2020/0281519 A1 | 9/2020 | Gowans et al. |
| 2020/0281529 A1 | 9/2020 | Grubb et al. |
| 2020/0281678 A1 | 9/2020 | Long et al. |
| 2020/0281775 A1 | 9/2020 | Kushnir et al. |
| 2020/0282100 A1 | 9/2020 | Gil et al. |
| 2020/0282114 A1 | 9/2020 | Long et al. |
| 2020/0282115 A1 | 9/2020 | Gardner et al. |
| 2020/0289328 A1 | 9/2020 | Luckemeyer et al. |
| 2020/0289347 A1 | 9/2020 | Gowans et al. |
| 2020/0289701 A1 | 9/2020 | Hall et al. |
| 2020/0289712 A1 | 9/2020 | Jiang et al. |
| 2020/0289723 A1 | 9/2020 | Gregory et al. |
| 2020/0289726 A1 | 9/2020 | Locke et al. |
| 2020/0289727 A1 | 9/2020 | Locke |
| 2020/0289806 A1 | 9/2020 | Locke et al. |
| 2020/0297541 A1 | 9/2020 | Hartwell et al. |
| 2020/0297543 A1 | 9/2020 | Rodzewicz et al. |
| 2020/0297544 A1 | 9/2020 | Moine et al. |
| 2020/0297892 A1 | 9/2020 | Silcock |
| 2020/0297893 A1 | 9/2020 | Ericson |
| 2020/0297894 A1 | 9/2020 | Koyama et al. |
| 2020/0299865 A1 | 9/2020 | Bonnefin et al. |
| 2020/0306089 A1 | 10/2020 | Delury et al. |
| 2020/0306091 A1 | 10/2020 | Lee et al. |
| 2020/0306094 A1 | 10/2020 | Kushnir et al. |
| 2020/0315853 A1 | 10/2020 | Waite |
| 2020/0315854 A1 | 10/2020 | Simmons et al. |
| 2020/0316271 A1 | 10/2020 | Lin |
| 2020/0323692 A1 | 10/2020 | Locke et al. |
| 2020/0324015 A1 | 10/2020 | Kettel et al. |
| 2020/0330283 A1 | 10/2020 | Locke et al. |
| 2020/0330284 A1 | 10/2020 | Locke et al. |
| 2020/0330285 A1 | 10/2020 | Rehbein et al. |
| 2020/0330658 A1 | 10/2020 | Fujisaki |
| 2020/0330660 A1 | 10/2020 | Patel et al. |
| 2020/0337719 A1 | 10/2020 | Ingram et al. |
| 2020/0337904 A1 | 10/2020 | Waite |
| 2020/0337905 A1 | 10/2020 | Earl et al. |

(56) References Cited

U.S. PATENT DOCUMENTS

| | | |
|---|---|---|
| 2020/0337906 A1 | 10/2020 | Long et al. |
| 2020/0337908 A1 | 10/2020 | Long et al. |
| 2020/0338228 A1 | 10/2020 | Kharkar et al. |
| 2020/0338243 A1 | 10/2020 | Harrison et al. |
| 2021/0236342 A1 | 8/2021 | Long et al. |
| 2021/0259889 A1 | 8/2021 | Holm et al. |
| 2021/0353472 A1 | 11/2021 | Allen et al. |
| 2021/0361854 A1 | 11/2021 | Askem et al. |
| 2021/0378872 A1 | 12/2021 | Gowans et al. |
| 2021/0378874 A1 | 12/2021 | Taylor et al. |
| 2021/0401628 A1 | 12/2021 | Gowans et al. |
| 2022/0000670 A1 | 1/2022 | Adie et al. |
| 2022/0023527 A1 | 1/2022 | Beadle et al. |
| 2022/0031231 A1 | 2/2022 | Hunt et al. |
| 2022/0062060 A1 | 3/2022 | Hu et al. |
| 2022/0080105 A1 | 3/2022 | Askem et al. |
| 2022/0096727 A1 | 3/2022 | Collinson et al. |
| 2022/0117795 A1 | 4/2022 | Adie et al. |
| 2022/0117796 A1 | 4/2022 | Adie et al. |
| 2022/0117797 A1 | 4/2022 | Adie et al. |
| 2022/0142822 A1 | 5/2022 | Cotton |
| 2022/0175587 A1 | 6/2022 | Wohlgemuth et al. |
| 2022/0183894 A1 | 6/2022 | Mumby et al. |
| 2022/0184269 A1 | 6/2022 | Maher et al. |
| 2022/0192886 A1 | 6/2022 | Hartwell et al. |

FOREIGN PATENT DOCUMENTS

| | | |
|---|---|---|
| EP | 3474799 B1 | 7/2021 |
| EP | 3182946 B1 | 8/2021 |
| EP | 3630031 B1 | 9/2021 |
| EP | 3628289 B1 | 11/2021 |
| EP | 3096728 B1 | 12/2021 |
| EP | 3104816 B1 | 12/2021 |
| EP | 3448451 B1 | 12/2021 |
| EP | 3681452 B1 | 12/2021 |
| EP | 3181160 B1 | 1/2022 |
| EP | 3288512 B1 | 1/2022 |
| EP | 3939554 A1 | 1/2022 |
| EP | 3142615 B1 | 2/2022 |
| EP | 3740179 B1 | 3/2022 |
| EP | 3406231 B1 | 4/2022 |
| EP | 3421020 B1 | 5/2022 |
| EP | 3315145 B1 | 6/2022 |
| EP | 4008299 A1 | 6/2022 |
| WO | 2005018543 A2 | 3/2005 |
| WO | 2011121394 A1 | 10/2011 |
| WO | 2011135284 A1 | 11/2011 |
| WO | 2011144888 A1 | 11/2011 |
| WO | 2013015827 A2 | 1/2013 |
| WO | 2013126049 A1 | 8/2013 |
| WO | 2014014842 A1 | 1/2014 |
| WO | 2015145117 A1 | 10/2015 |
| WO | 2015173546 A1 | 11/2015 |
| WO | 2016141450 A1 | 9/2016 |
| WO | 2017016974 A1 | 2/2017 |
| WO | 2017125250 A1 | 7/2017 |
| WO | 2018029231 A1 | 2/2018 |
| WO | 2018094061 A1 | 5/2018 |
| WO | 2018162613 A1 | 9/2018 |
| WO | 2018163093 A1 | 9/2018 |
| WO | 2018189265 A1 | 10/2018 |
| WO | 2018226667 A1 | 12/2018 |
| WO | 2018227144 A1 | 12/2018 |
| WO | 2018231825 A1 | 12/2018 |
| WO | 2018236648 A1 | 12/2018 |
| WO | 2019002085 A1 | 1/2019 |
| WO | 2019012068 A1 | 1/2019 |
| WO | 2019012069 A1 | 1/2019 |
| WO | 2019022493 A1 | 1/2019 |
| WO | 2019027933 A1 | 2/2019 |
| WO | 2019038548 A1 | 2/2019 |
| WO | 2019038549 A1 | 2/2019 |
| WO | 2019040656 A1 | 2/2019 |
| WO | 2019050855 A1 | 3/2019 |
| WO | 2019058373 A1 | 3/2019 |
| WO | 2019073326 A1 | 4/2019 |
| WO | 2019083563 A1 | 5/2019 |
| WO | 2019083868 A1 | 5/2019 |
| WO | 2019086911 A1 | 5/2019 |
| WO | 2019091150 A1 | 5/2019 |
| WO | 2019094147 A1 | 5/2019 |
| WO | 2919096828 A1 | 5/2019 |
| WO | 2019113275 A1 | 6/2019 |
| WO | 2019113623 A1 | 6/2019 |
| WO | 2019191590 A1 | 10/2019 |
| WO | 2019193141 A1 | 10/2019 |
| WO | 2019193333 A1 | 10/2019 |
| WO | 2019199389 A1 | 10/2019 |
| WO | 2019199596 A1 | 10/2019 |
| WO | 2019199687 A1 | 10/2019 |
| WO | 2019199798 A1 | 10/2019 |
| WO | 2019199849 A1 | 10/2019 |
| WO | 2019200035 A1 | 10/2019 |
| WO | 2019215572 A1 | 11/2019 |
| WO | 2019219613 A1 | 11/2019 |
| WO | 2019234365 A1 | 12/2019 |
| WO | 2020005062 A1 | 1/2020 |
| WO | 2020005344 A1 | 1/2020 |
| WO | 2020005536 A1 | 1/2020 |
| WO | 2020005546 A1 | 1/2020 |
| WO | 2020005577 A1 | 1/2020 |
| WO | 2020007429 A1 | 1/2020 |
| WO | 2020011691 A1 | 1/2020 |
| WO | 2020014178 A1 | 1/2020 |
| WO | 2020014310 A1 | 1/2020 |
| WO | 2020018300 A1 | 1/2020 |
| WO | 2020026061 A1 | 2/2020 |
| WO | 2020026144 A1 | 2/2020 |
| WO | 2020033351 A1 | 2/2020 |
| WO | 2020035811 A1 | 2/2020 |
| WO | 2020043665 A1 | 3/2020 |
| WO | 2020044237 A1 | 3/2020 |
| WO | 2020046443 A1 | 3/2020 |
| WO | 2020047255 A1 | 3/2020 |
| WO | 2020049038 A1 | 3/2020 |

* cited by examiner

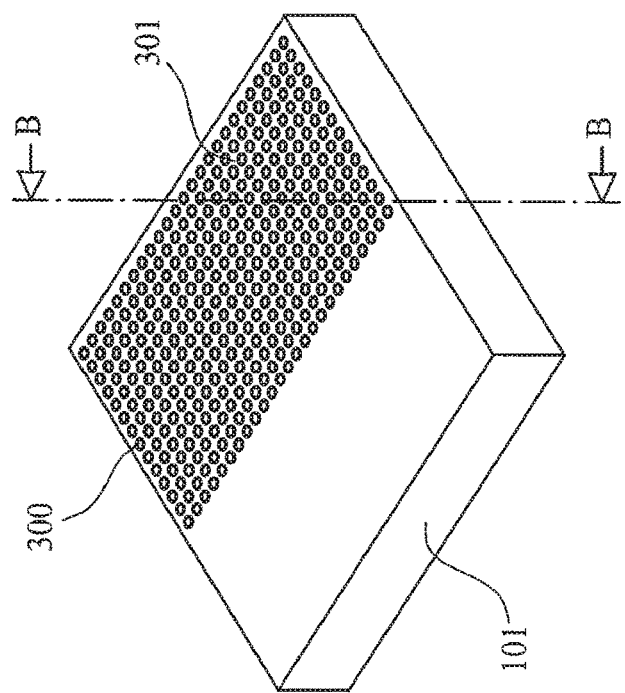
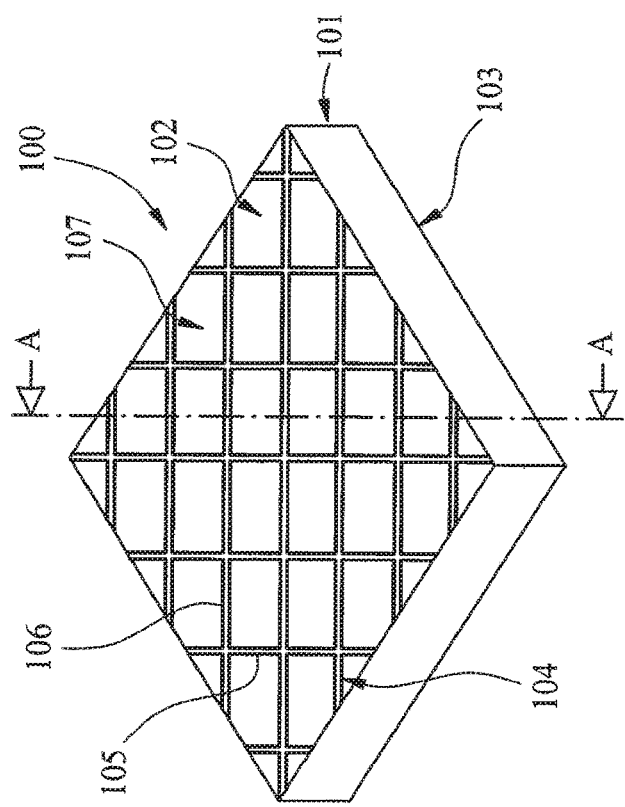
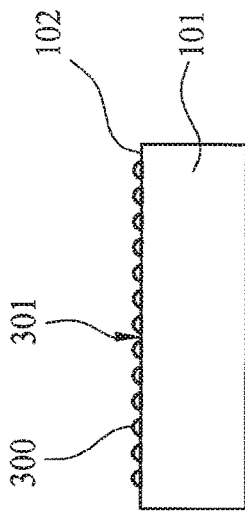

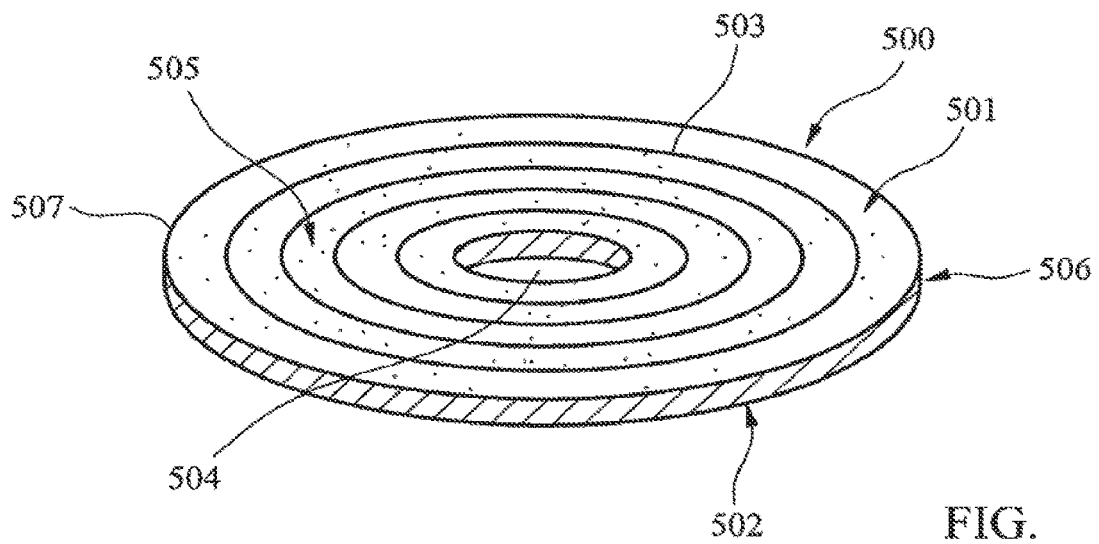
FIG. 5
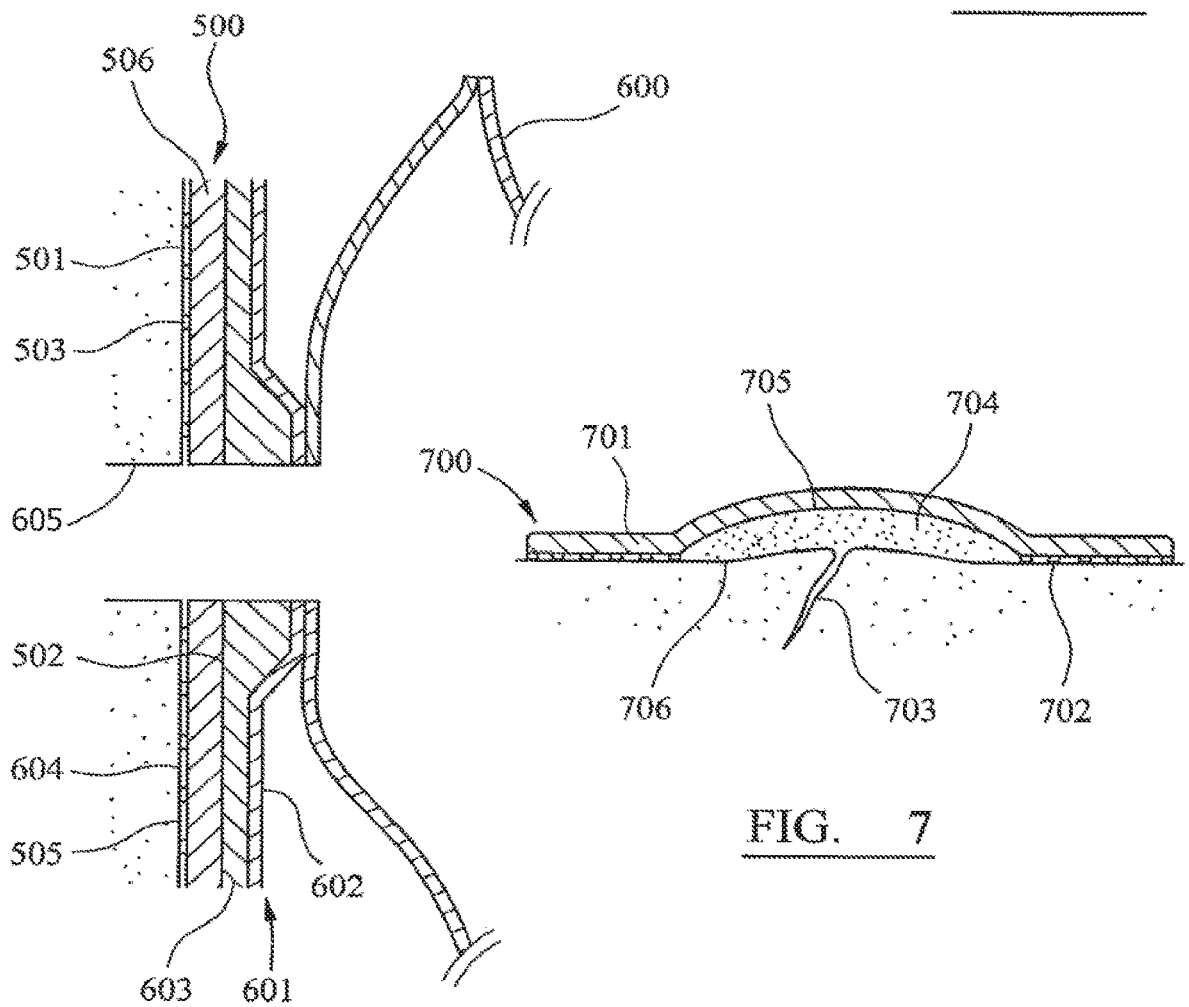
FIG. 7
FIG. 6

SKIN CONTACT MATERIAL

CROSS-REFERENCE

This application is a continuation of U.S. application Ser. No. 14/347,966, filed Jul. 14, 2014, which is a U.S. National Phase of PCT/GB2012/052132, filed Aug. 31, 2012, which claims the benefit of priority of GB 1115182.6, filed Sep. 2, 2011, each of which is incorporated herein by reference in their entirety.

BACKGROUND OF THE INVENTION

The present invention relates to a skin contact material for positioning against a human or animal skin and in particular, although not exclusively, to a material suitable for ostomy use, wound care and as a medical dressing and adhesive.

Self-adhering skin contact materials find widespread use in the medical field and in particular with ostomy appliances. Initially, medical grade pressure-sensitive adhesives, typically formed from an acrylic, were used to adhere appliances to the peristomal skin of a patient. More recently, moisture absorbing, and in particular hydrocolloid containing, skin barrier materials have emerged as more suitable skin contact materials. These materials absorb moisture from the skin and allow the skin to breathe whilst being sufficiently tacky for good skin adhesion but being easily peeled away without irritating or damaging the skin.

Skin friendly adhesive barrier materials are disclosed in U.S. Pat. No. 3,339,546; U.S. Pat. No. 4,477,325; U.S. Pat. No. 4,738,257 and U.S. Pat. No. 4,867,748.

However, hydrocolloid based substrates may not possess the required adhesive characteristics for certain skin contact applications and an additional adhesive may be required. The problem with medical grade adhesives is that they tend to be skin irritants following extended use. In particular, and as a generalisation, they do not allow the same level of moisture transfer with the skin.

What is required therefore is a medical grade skin contact material for use as a barrier layer and/or a means of attaching appliances to the skin that comprise the required adhesive properties whilst allowing moisture transfer with the skin.

Accordingly, the inventors provide a substrate based skin contact material preferably formed from a hydrocolloid having a silicone based adhesive component extending over regions of the substrate surface. The adhesive is formed non-continuously over the hydrocolloid so as to provide areas of the hydrocolloid that are devoid of the silicone adhesive. Accordingly, with the material in contact with the skin, adhesion is provided via the silicone adhesive whilst the areas of exposed hydrocolloid are capable of moisture transfer so as to significantly improve the skin friendliness of the material during use and allow the material to be readily removed from the skin without causing irritation.

BRIEF SUMMARY OF THE INVENTION

According to a first aspect of the present invention there is provided a skin contact material for positioning against human or animal skin, the material comprising: a hydrocolloid substrate having a first surface intended to be positioned against the skin and a second surface intended to be facing away from the skin; a silicone adhesive layer provided on the first surface and intended to be positioned in contact with the skin to adhere the material to the skin, the silicone adhesive layer being non-continuous over the first surface such that areas of the first surface are not concealed by the silicone adhesive layer, the areas capable of positioning directly adjacent and/or in contact with the skin.

The hydrocolloid substrate may comprise a synthetic or natural hydrocolloid, such as a hydrocolloid derived from natural sources. The hydrocolloid may comprise anyone or a combination of a gum, a cellulose or cellulose derivative, an alginate or a starch.

Optionally, the hydrocolloid comprises gelatine or pectin. Optionally, the hydrocolloid comprises a carboxymethylcellulose in a polyisobutylene matrix. Alternatively, the substrate may be non-hydrocolloid based and may comprise low density polyethylene, high density polyethylene, polypropylene, polyester or a silicone based material. Alternatively the substrate could be a composite of two or more different materials including polymers and hydrocolloids.

Preferably, the silicone adhesive comprises a two part catalysed, low temperature curing silicone elastomer. As will be appreciated, the silicone adhesive may be formed as a composite of a plurality of different silicones and/or silicone based materials.

Optionally, the skin contact material may be provided as a sheet or roll from which a user or medical practitioner may cut the desired shape and size. Moreover, the hydrocolloid substrate may comprise a thickness in the range 0.5 to 5.0 mm.

As indicated, the enhanced skin friendliness of the present material is provided by layering the silicone adhesive upon the substrate at discrete regions so as to provide areas of exposed substrate for positioning in contact with the skin. Accordingly, the silicone adhesive may be formed as lines or dots on the skin contact surface of the substrate.

Where the adhesive layer is formed as individual dots, flecks or marks, the pattern created by these dots may be uniform across the surface of the substrate. Alternatively, the pattern may change over the substrate surface and the material may comprise different patterns at different regions over the substrate. Where the adhesive layer comprises lines or ridges extending over the substrate, these lines may extend in different directions where the spacing between the lines or ridges is the same or variable across the substrate surface. Optionally, the lines may create a square, rectangular or circular grid pattern. Preferably, for ostomy applications, the silicone adhesive is bonded to the substrate and takes the form of concentric circles extending around a central aperture extending through the substrate.

According to a second aspect of the present invention there is provided a medical dressing comprising a skin contact material as described herein. According to a third aspect of the present invention there is provided a stoma gasket comprising a skin contact material as described herein. According to a fourth aspect of the present invention there is provided a medical adhesive pad, tape or sheet comprising a skin contact material as described herein. According to a fifth aspect of the present invention there is provided a skin barrier pad for positioning about a stoma comprising a skin contact material as described herein. According to a sixth aspect of the present invention there is provided an ostomy bag comprising a skin contact material as described herein.

According to a seventh aspect of the present invention there is provided a skin contact material for positioning against human or animal skin, the material comprising: a substrate having a first surface intended to be positioned against the skin and a second surface intended to be facing away from the skin, the substrate comprising any one or a combination of a hydrocolloid, a low density polyethylene, a high density polyethylene, a polypropylene, a polyester or a silicone based material; a silicone adhesive layer provided on the first surface and intended to be positioned in contact with the skin to adhere the material to the skin, the silicone adhesive layer being non-continuous over the first surface such that areas of the first surface are not concealed by the silicone adhesive layer, the areas capable of positioning directly adjacent and/or in contact with the skin.

BRIEF DESCRIPTION OF THE DRAWINGS

A specific implementation of the present invention will now be described, by way of example only, and with reference to the accompanying drawings in which:

FIG. 1 is perspective view of a skin contact material having a substrate and an adhesive component bonded to one face of the substrate according to the specific implementation;

FIG. 2 is a cross section to A-A of FIG. 1;

FIG. 3 is a perspective view of a further specific implementation of the skin contact material of FIG. 1;

FIG. 4 is a cross section through B-B to FIG. 3;

FIG. 5 is a perspective view of a stoma gasket formed from the skin contact material according to a specific implementation;

FIG. 6 contains a cross sectional side view of the stoma gasket at an adhesive ring of FIG. 5 secured in position against a patient's skin and in contact with a flange of an ostomy bag;

FIG. 7 is a cross sectional side view of the skin contact material used as a wound dressing adhesive to maintain a dressing in position over a wound at the skin.

DETAILED DESCRIPTION OF THE INVENTION

Figure 8:
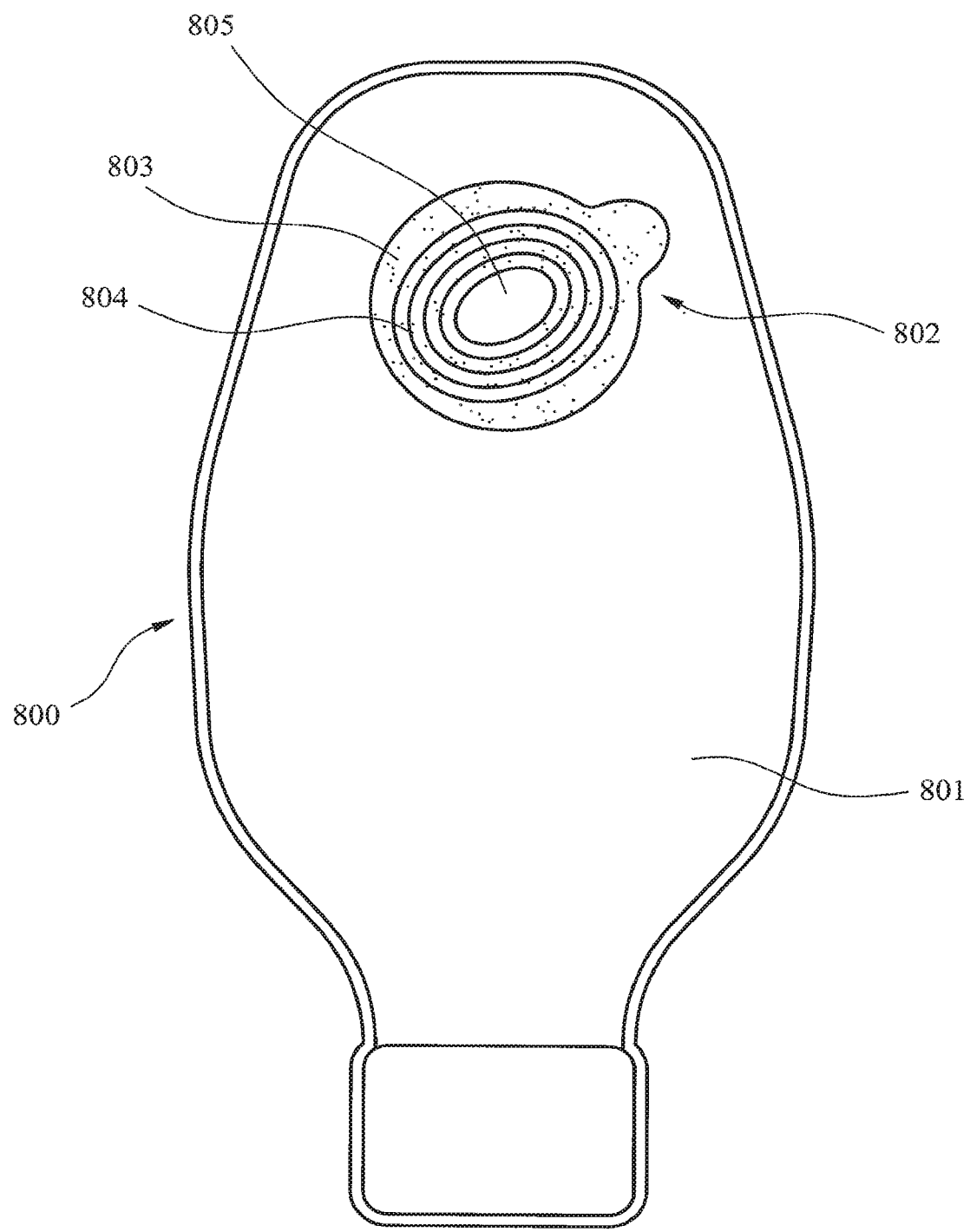
FIG. 8 is a side view of an ostomy bag having a flange comprising the skin contact material according a specific implementation.

Referring to FIGS. 1 and 2, the skin contact material 100 comprises a substrate 101 having a first surface 102 intended to be facing the skin and an opposed second surface 103 intended to be facing away from the skin. An adhesive layer 104 is provided on the surface 102 and according to the specific implementation, layer 104 comprises a rectangular grid pattern formed by perpendicular aligned ridges 105, 106.

Adhesive layer 104, formed from the narrow ridges 105, 106 is regarded as 'discontinuous' over surface 102 such that the adhesive 104 does not coat completely surface 102 and there is provided regions 107 that are devoid of adhesive 104 with regions 107 being exposed substrate 102. The rectangular grid pattern formed by ridges 105, 106 is uniform across surface 102 such that the space between ridges 105, 106 is equal in the respective directions across substrate surface 102. According to the specific implementation, the thickness of substrate 101 is in range 0.5 to 5.0 mm. The distance by which ridges 105, 106 extend from surface 102 is a small percentage of this thickness and may be of the order of 0.01 mm.

FIGS. 3 and 4 illustrate a further embodiment of the skin contact material of FIGS. 1 and 2. According to the further embodiment, the adhesive layer is formed as a regular repeating array of nodes or bumps 300. The bumps 300 are separated from one another by a regular or uniform discreet separation distance such that the skin contact surface 102 of substrate 101 is exposed at spacings 301 between the bumps 300.

The material of the embodiment of FIGS. 1 to 4 is suitable for use as a medical grade skin contact material and in particular a material for adherence to the skin of colostomy, ileostomy and urostomy appliances. The material is also suitable for adherence to the skin of patient monitoring appliances, prosthetics and wound dressings.

Specifically with regard to ostomy applications, FIG. 5 illustrates a specific embodiment of the skin contact material 500 formed as an annular disc suitable for use as a skin contact stoma gasket. The skin contact material 500 comprises a central aperture or bore 504 extending through skin contact material 500. Skin contact material 500 comprises a substrate 506 having a skin contact surface 501 and opposed surface 502 intended to be facing away from the skin. An adhesive layer 503 is provided on the surface 501 and is formed as a series of concentric circles extending between central bore 504 and parameter edge 507. The concentric circles of the adhesive layer 503 are spaced apart from one another and therefore formed as discreet ridges separated by regions 505 of exposed substrate surface 501.

FIG. 6 illustrates the skin contact material 500 of FIG. 5 secured in position at the peristomal skin 604. The adhesive ridges of the adhesive layer 503 are positioned in contact with the peristomal skin 604 such that regions 505 are in a position very close to or in direct contact with skin 604 so as to provide moisture transfer between skin contact material 500 and skin 604. That is, moisture is actively transferred from skin 604 and into material 500 via regions 505. This would otherwise not be possible if adhesive layer 503 extended continuously over skin contact surface 501.

An ostomy bag 600 comprises a flange 601 formed from a solid support 602 that supports an attachment flange 603. Bag 600 is secured to the skin 604 indirectly by mating attachment 603 with the opposed surface 502 of skin contact material 500. Central bore 504 of skin contact material 500 is appropriately sized to fit around stoma 605 and allow the free passage of excreted matter into bag 600. The ostomy bag 600 and the skin contact material 500 may be readily removed from the peristomal skin 604 by simply pilling-away the skin contact material 500.

FIG. 7 illustrates a further use of the present skin contact material as a wound dressing. The wound dressing 700 comprises a substrate 701 and an adhesive layer 702 incompletely formed across the skin contact surface of substrate 701. According to the further embodiment, adhesive layer 702 may be formed at an outer perimeter region of the substrate so as to provide a central region 705 that is devoid of adhesive 702.

Alternatively, adhesive layer 702 may extend across the entire skin facing surface of substrate 701 but importantly comprising regular repeating regions that are devoid of the adhesive layer. The wound dressing 700 is configured to retain a second wound dressing material 704 in contact with the skin 706 surrounding the region of a wound 703. Due to the moisture transfer capability of substrate 701, the skin 706 at the region in contact with the pad 700, is allowed to breathe and does not become irritated by this contact.

According to further embodiments, the silicone adhesive layer 104, 300, 503, 702 may also be provided on the second surface of the substrate 103, 502 intended to be facing away from the skin. This second opposed adhesive layer may have the same or a different configuration to the skin contact adhesive layer on the first surface. Also, this second and opposed adhesive layer may have a uniform configuration across the second surface 103, 502 or the configuration may be different at different regions on surface 103, 502 as described with references to the first adhesive layer detailed in FIGS. 1 to 7.

FIG. 8 illustrates an ostomy bag 800 having an internal chamber 801 to receive excreted matter. An attachment flange 802 provides an interface between the chamber 801 and a stoma whilst providing a means of attachment of the bag 800 to the peristomal skin. The present skin contact material is formed as a permanent or releasable part of flange 802 and extends around a central aperture 805 for positioning around the stoma. Flange 802 comprises a substrate 803 with moisture transfer characteristics as described with reference to FIGS. 1 to 7. A silicone adhesive layer 804, as described herein, is formed as discrete concentric circles on the skin facing side of flange 802 and extends around the central aperture 805 as described with reference to FIG. 5.

According to further specific implementations the substrate may be non-hydrocolloid based and may comprise medical grade polymers such as polyalkylenes, polyesters and/or silicone based materials.

According to a first example the substrate may comprise a low density polyethylene. Suitable low density polyethylene materials include those available from Dow Corning, MI, USA under the product range Dow™ LDPE.

According to a second example the substrate may comprise a high density polyethylene. Suitable materials include those available from Dow Corning, MI, USA under the product range Dow™ HDPE or materials under the product range Eraclene™ HDPE available from Polimeri Europa, ENI Rome, Italy.

According to a third example the substrate may comprise a polypropylene material. Suitable materials include those available from Westlake Plastics Company, PA, USA under the product range Propylux™ HS.

According to a fourth example the substrate may comprise a polyester material. Suitable materials include polyesters available from Bayer MaterialScience LLC, PN, USA under the product range Texin™ RxHM125.

According to a fifth example, the substrate may comprise a silicone based material. Suitable materials include those available from Dow Corning, MI, USA under the product range Silastic™ and the Class VI Elastomers under the product range C-6.

As will be appreciated, the different types of substrate according to the further examples are bondable to the adhesive layer according to conventional bonding techniques and processes as described with reference to the previous embodiments.

What is claimed is:

1. A skin contact material for positioning against human or animal skin, the material comprising:
    a hydrocolloid substrate having a first surface intended to be positioned against the skin and a second surface intended to be positioned away from the skin;
    a two part catalysed, low temperature curing silicone adhesive layer coated on the first surface and configured to contact and adhere the material to the skin, wherein the two part catalysed, low temperature curing silicone adhesive layer is non-continuous over the first surface such that areas of the first surface are not concealed by the two part catalysed, low temperature curing silicone adhesive layer, wherein the areas are capable of positioning in contact with the skin, wherein the two part catalysed, low temperature curing silicone adhesive layer is coated on the first surface as a rectangular grid pattern formed by a plurality of protrusions extending over the first surface, wherein the plurality of protrusions are coated on a flat face of the first surface that is devoid of projections, wherein the plurality of protrusions include a first set of protrusions aligned in protrusion rows that are spaced apart from one another in a first direction such that the protrusion rows are not directly interconnected with one another and a second set of protrusions aligned in protrusion columns that are spaced apart from one another in a second direction perpendicular to the first direction such that the protrusion columns are not directly interconnected with one another, wherein the protrusion rows extend perpendicular to the protrusion columns over the flat face of the first surface, wherein the first set of protrusions are aligned in each protrusion row with discontinuities located between adjacent protrusions, wherein the second set of protrusions are aligned in each protrusion column with discontinuities located between adjacent protrusions, wherein the plurality of protrusions are formed as bumps or dots, wherein the plurality of protrusions are coated non-uniformly over the first surface of the substrate, wherein the first surface of the substrate includes a first side and a second side arranged opposite the first side, and wherein the plurality of protrusions are coated only on the first side of the first surface without being coated on the second side of the first surface.

2. The material as claimed in claim 1 wherein the hydrocolloid substrate comprises a synthetic material.

3. The material as claimed in claim 1 wherein the hydrocolloid substrate comprises a natural hydrocolloid.

4. The material as claimed in claim 3 wherein the natural hydrocolloid comprises any one or a combination of the following set of:
    a gum;
    a cellulose;
    a cellulose derivative;
    an alginate; and
    a starch.

5. The material as claimed in claim 1 further comprising gelatin or pectin.

6. The material as claimed in claim 1 wherein the hydrocolloid substrate further comprises a carboxymethylcellulose in a polyisobutylene matrix.

7. The material as claimed in claim 1 wherein the two part catalysed, low temperature curing silicone adhesive layer is a composite and comprises a plurality of different silicones and/or silicone based materials.

8. The material as claimed in claim 1 wherein the hydrocolloid substrate comprises a thickness in the range 0.5 to 5.0 mm.

9. The material as claimed in claim 1 wherein the plurality of protrusions create a pattern on the first surface that is substantially non-uniform over the first surface such that the two part catalysed, low temperature curing silicone adhesive layer comprises a plurality of different patterns at different regions of the hydrocolloid substrate.

10. A medical device comprising a skin contact material according to claim 1, wherein the medial device is selected from the group consisting of a medical dressing, a stoma gasket, a medical adhesive pad, tape, or sheet, a stoma skin barrier pad, and an ostomy bag.

11. A skin contact material for positioning against human or animal skin, the material comprising:
    a substrate having a first surface intended to be positioned against the skin and a second surface intended to be positioned away from the skin, the substrate comprising any one or a combination of a hydrocolloid, a low density polyethylene, a high density polyethylene, a polypropylene, a polyester, or a silicone based material;

a two part catalysed, low temperature curing silicone adhesive layer coated on the first surface and configured to contact and adhere the material to the skin, wherein the two part catalysed, low temperature curing silicone adhesive layer is non-continuous over the first surface such that areas of the first surface are not concealed by the two part catalysed, low temperature curing silicone adhesive layer, wherein the areas are capable of positioning in contact with the skin, wherein the two part catalysed, low temperature curing silicone adhesive layer is coated on the first surface as a repeating array of nodes or bumps, wherein the array of nodes or bumps are coated on a flat face of the first surface that is devoid of projections, wherein the array of nodes or bumps includes a first set of nodes or bumps disposed parallel to one another in a first plurality of discontinuous lines and a second set of nodes or bumps disposed parallel to one another in a second plurality of discontinuous lines, and wherein the first set of nodes or bumps are disposed perpendicular to the second set of nodes or bumps, wherein the first surface of the substrate includes a first side and a second side arranged opposite the first side, and wherein the array of nodes or bumps are coated only on the first side of the first surface without being coated on the second side of the first surface such that the array of nodes or bumps are coated non-uniformly over the first surface.

12. The material of claim 11, wherein the two part catalysed, low temperature curing silicone adhesive layer is a composite and comprises a plurality of different silicones and/or silicone based materials.

13. The material of claim 11, wherein the substrate comprises a hydrocolloid having a thickness in the range 0.5 to 5.0 mm.

14. The material of claim 11, wherein the array of nodes or bumps are uniformly separated from one another by a separation distance.

15. The material of claim 11, wherein the array of nodes or bumps are coated on half of a total surface area of the first surface.

16. The material of claim 11, wherein each of the first side and the second side accounts for half of a total surface area of the first surface.

* * * * *